US007008651B2

(12) United States Patent
Ambuel et al.

(10) Patent No.: US 7,008,651 B2
(45) Date of Patent: Mar. 7, 2006

(54) E. COLI EXTRACT FOR PROTEIN SYNTHESIS

(75) Inventors: Yuping Ambuel, Madison, WI (US); Thomas R. Van Oosbree, Madison, WI (US); Mark R. McCormick, Madison, WI (US); Robert C. Mierendorf, Madison, WI (US)

(73) Assignee: EMD Biosciences, Inc., San Diego, CA (US)

( * ) Notice: Subject to any disclaimer, the term of this patent is extended or adjusted under 35 U.S.C. 154(b) by 508 days.

(21) Appl. No.: 09/848,449

(22) Filed: May 3, 2001

(65) Prior Publication Data

US 2002/0034559 A1    Mar. 21, 2002

Related U.S. Application Data

(60) Provisional application No. 60/201,450, filed on May 3, 2000.

(51) Int. Cl.
  A61K 35/66  (2006.01)
  A61K 35/68  (2006.01)
  C12P 21/06  (2006.01)
  A01N 63/02  (2006.01)
(52) U.S. Cl. .................... 424/780; 435/243; 435/252.8; 424/780
(58) Field of Classification Search ................ 424/780; 435/243, 252.8
  See application file for complete search history.

(56) References Cited

OTHER PUBLICATIONS

"Promega Protocols and Applications Guide" Second Ed Mar. 1991 pp. 157, 166-167.*
Alberts et al., "DNA-Celluose Chromatography," *Resolution of Nucleic Acids* 11:198-217 ( ).
Gross, et al., "Rapid Micromethod for the Purification of *Escherichia coli* Ribonucleic Acid Polymerase and the Preparation of Bacterial Extracts Active in Ribonucleic Acid Synthesis," *Journal of Bacteriology* 128:382-389 (1976).
Kang, et al., "An efficient cell-free protein synthesis system using periplasmic phosphataase-removed S30 extract," *Journal of Microbiological Methods* 43:91-96 (2000).
Kawarasaki, et al., "Phosphatase-immunodepleted cell-free protein synthesis system," *Journal of Biotechnology* 61:199-208 (1998).
Kigawa, et al., "Cell-free production and stable-isotope labeling of milligram quantities of proteins," *1FEBS Letters* 442:15-19 (1999).
Kim et al., "A highly efficient cell-free protein synthesis system from *Escherichia coli*," *Eur J. Biochem* 239(3): 881-886 (1996).
Kuriki, Yoshitaka, "Stimulation in Vitro of Expression of the AMP Gene of pBR322 by Soluble Protein Fractions Isolated From E. Coli.," *Biochemistry International* 12:593-602 (1986).
Lesley, et al., "Use of in Vitro Protein Synthesis from Polymerase Chain Reaction-generated Templates to Study Interaction of *Escherichia coli* Transcription Factors with Core RNA Polymerase and for Epitope Mapping of Monoclonal Antibodies," *The Journal of Biological Chemistry*, 266:2632-2638 (1991).
Lesley, S. A., "Preparation and Use of *E. Coli* S-30 Extracts," *Methods in Molecular Biology* 37:265-278 (1995).
Liou, et al., "RNA degradosomes exist in vivo in *Escherichia coli* as multicomponent complexes associate with the cytoplasmic membrane via the N-terminal region of ribonuclease E," *PNAS* 98:63-96 (2001).
Lopez et al., "The C-terminal half of RNase E, which organizes the *Escherichia coli* degradosome, participates in mRNA degradation but not rRNA processing in vivo," *Molecular Microbiology* 33:188-199 (1999).
Nakano, et al., "Highly productive cell-free protein synthesis system using condensed wheatgerm extract," *Journal of Biotechnology* 46:275-282 (1996).
Patnaik et al., "*E. coli*-Based In Vitro Transcription/Translation: In Vivo-Specific Synthesis Rate and High Yields in a Batch System," *BioTechniques* 24:862-868 (1998).
Pratt, J.M., "Coupled Transcription-Translation in Prokaryotic Cell-Free Systems," *Transcription and Translation IRL Press* (1984).
"*E. coli* S30 Extract System for Circular DNA," *Promega Technical Bulletin* (1998).
"*E. coli* T7 S30 Extract System for Circular DNA," *Promega Technical Bulletin* (1995).
"Proteinscript-PRO™, "*Ambion, Inc. Technical Bulletin* —.
*E. Coli* S30 Extract System for Linear Templates, *Promega Technical Bulletin* (1998).

(Continued)

Primary Examiner—Herbert J. Lilling
(74) Attorney, Agent, or Firm—Foley & Lardner LLP (57) ABSTRACT

There is now a market for kits containing the necessary components for performing protein synthesis reactions using template DNA of the experimenter. One category of existing system for performing protein synthesis reactions is based on an S-30 extract from the bacteria *E. coli*. It is disclosed here that a simple fractionation process can dramatically improve the performance of an S-30 prokaryotic protein synthesis reaction mixture. In one embodiment, the fractionation is a simple freezing and thawing of an S-30 extract combined with a supplemental mix, followed by centrifugation. The resulting fractionated S-30 reaction mixture yields more full-length target protein and less non-full length or non-target protein than possible using prior art S-30 systems.

17 Claims, 7 Drawing Sheets

OTHER PUBLICATIONS

Shibuya, et al., "Studies on Stringent Control in a Cell-Free System," *J. Biochem.* 86:403-411.

Vanzo et al., "Ribonuclease E. organizes the protein interactions in the *Escherichia coli* RNA degradosome," *Genes & Development* 12:2770-2781 (1998).

Chen, et al., "Prokaryotic Coupled Transcription-Translation," *Methods in Enzymology* 101:674 (1983).

Zubay, G., "In Vitro Synthesis of Protein in Microbial Systems," 267-287 (1973).

* cited by examiner

Anti-RNase E

E. COLI EXTRACT FOR PROTEIN SYNTHESIS

CROSS-REFERENCE TO RELATED APPLICATIONS

This application claims the benefit of U.S. Provisional Application No. 60/201,450 filed May 3, 2000. This application is incorporated herein by reference in its entirety.

STATEMENT REGARDING FEDERALLY SPONSORED RESEARCH OR DEVELOPMENT

Not applicable.

BACKGROUND OF THE INVENTION

The techniques of modern biotechnology have made possible the identification of the genetic elements, or genes, which control the characteristics of living organisms. The principle manner by which most genes cause effects in organisms is by encoding the construction of proteins. Thus in studying genes, it is often desired to produce a protein from the protein coding DNA from the gene, to study what the protein is, or what the protein does, or to perform some useful reaction with the protein. Sometimes a protein is expressed by inserting the entire gene, or an artificial construct carrying the protein coding sequence in an expression vector, into a suitable host cell so that the host cells can be grown to produce the protein. Another technique is to produce the protein in vitro directly from a gene or an artificial genetic construct in a cell free protein synthesis process. In vitro techniques for protein synthesis have the advantage that the protein can be produced directly from the encoding DNA without the necessity for intermediate culture and proliferation of transformed cells. In vitro protein synthesis provides the further advantage of allowing the production of proteins that are typically difficult or impossible to express in living cells, such as toxins or proteins containing amino acids that do not normally occur in living cells.

Methods for in vitro transcription and translation of DNA to produce protein have been known for many years. The earliest documented descriptions of in vitro protein synthesis were developed in prokaryotic systems that utilized bacterial transcriptional and translational components to produce proteins in a coupled reaction. A common prokaryotic system, known as an *E. coli* S-30 cell free extract, was first described in a systematic way by Zubay, *Annual Review of Genetics* 7:267–287 (1973). Others have written articles and reviews on how to better make and use such S-30 extracts. In addition, kits for the in vitro production of proteins from DNA have been commercialized based on the use of S-30 extracts. Such kits are sold by several manufacturers. More recently, systems have been developed for transcription and translation using eukaryotic cell free extracts, particularly those based on the use of rabbit reticulocyte lysate or wheat germ extract. U.S. Pat. Nos. 5,324,637 and 5,895,753 describe systems for in vitro transcription and translation of protein.

Both prokaryotic and eukaryotic cell free extracts for transcription and translation are sold today in commerce. In general, the researcher using an in vitro transcription and translation system wants the process to produce an optimum amount of the full length target protein and wants to minimize the amount of non-targeted protein and/or less than full length protein which is made. While prokaryotic systems are inherently simpler to use, the eukaryotic systems are thought to be superior for some applications. In particular, *E. coli* S-30 extracts are convenient to make and use but tend to produce a greater percentage of non-fill length protein than eukaryotic extracts. The production of unwanted protein or polypeptide products is generally observed by the presence of a variety of proteins different in size than the full-length target protein when the reaction products are visualized by gel electrophoresis. The non-full length proteins are thought to arise from several sources, which fall into two primary categories.

First, a certain amount of background non-target proteins is produced in S-30 systems due to transcription from other *E. coli* promoters present in the extract, either from residual *E. coli* genomic DNA left in the extract or from other promoters on plasmids or other vectors which carry the target gene. For example, most plasmids carry a gene which encodes a protein, such as β-lactamase, that confers resistance to a selective drug, such as ampicillin, in addition to the target gene. When such a plasmid is used as the template for in vitro protein synthesis in an *E. coli* S-30 extract, both the target gene and the drug resistance gene are transcribed by the RNA polymerase and protein is therefore produced from both genes. A minor amount of non-target background may also be derived from non-specific initiation of transcription of *E. coli* RNA polymerase on non-promoter sites on DNA present in the extract. This phenomenon is known to occur under some conditions but is unlikely to be significant under the typical reaction conditions for in vitro protein synthesis. Background can also be derived from translation of residual *E. coli* mRNA present in the extract. Some of the strategies that have been used to minimize the contribution of endogenous DNA and mRNA to non-target background include a pre-incubation step to allow run-off of ribosomes engaged in translation of endogenous mRNA and treatment with $Ca^{2+}$ dependent nuclease to preferentially degrade endogenous DNA and mRNA. However, it has not generally been possible to entirely eliminate or remove non-target synthesis with these steps, since some DNA and mRNA typically remains after the treatment, and extended incubation or over-treatment with nuclease results in unacceptably low levels of protein synthesis activity, presumably due to damage to other species of RNA, including rRNA and tRNA that participate in protein synthesis. A different approach has been taken to direct the exclusive synthesis of target proteins by using T7 RNA polymerase for transcription in *E. coli* extracts in the presence of rifampicin to inhibit *E. coli* RNA polymerase (Nevins and Pratt, *FEBS Lett* 291:259–263(1991)).

The second major category of background in *E. coli* extracts results in the generation of smaller, truncated forms of the target protein. These forms arise from one or more causes, including: (1) initiation of protein synthesis at internal AUG start codons other than the authentic N-terminal AUG, (2) synthesis of incomplete polypeptide chains due to premature termination of translation, (3) degradation of template DNA and/or RNA transcripts by nucleases present in the extract, and (4) degradation of the target protein by proteases present in the extract. The degradation of linear DNA templates has been approached by using extracts derived from strains deficient in one or more enzymes of the RecBCD complex (Yang et al., *Proc. Natl. Acad. Sci. USA* 77:7029–7033 (1980)). Strains deficient in ompT and lon proteases have also be used to minimize proteolytic degradation (Kohrer et al., *Eur. J. Biochem.* 236:234–239 (1996)). While these examples appear to alleviate some degradation activity, there are many additional activities in cells that have not been possible to eliminate due to their being essential for cellular viability. In addition, there is not a method currently known in the art that generally addresses internal initiation or premature termination, which are believed to be significant causes of non-full length background. One may imagine that the use of stains deficient in one or more of the major ribonuclease activities present in *E. coli* may produce extracts exhibiting greater synthesis of full length proteins, but there have been no reports of success using this approach. The various RNA degradation pathways in *E. coli* and the interactions of enzymes and other proteins involved therein, both in vivo and in vitro, are still being elucidated.

An important contributor to the degradation of RNA transcripts in cells appears to be the RNA degradosome, a multi-protein complex that is involved in RNA turnover and metabolism. The degradosome is organized around the enzyme RNase E which contains binding sites for other key protein components of the complex. See, for example, Lopez et al., *Mol. Micro.* 33(1). 189–199 (1999) and Vanzo et al., *Genes & Develop.* 12:2770–2781 (1998). What, if any, role the RNA degradosome or RNase E plays in *E coli* transcription and translation extracts was heretofore unknown.

The cell free S-30 system, as devised by Zubay and modified by others, traditionally involves the preparation of an extract and a supplemental mix. The extract contains all the enzymes and factors from the *E. coli* necessary for transcription and translation. The supplemental mix includes nucleotide triphosphates, tRNA, amino acids and an energy regenerating system plus certain co-factors and salts and ions. The making and using of such extracts and supplemental mixes has been documented for more than 30 years and have been sold as kits by commercial companies for some time. While such extracts are conventionally made using *E. coli*, there is no technical reason why such extracts cannot be made from any number of possible prokaryotic hosts.

A typical S-30 extract is made by first culturing the *E. coli* cells and harvesting them. The *E. coli* cells are then lysed or broken with a French pressure cell or other cell disruption device. The resulting lysate is then centrifuged to remove the cellular debris and other solid matter and the supernatant is saved for further processing. The supernatant is then combined with a pre-incubation buffer and incubated. Sometimes a microccocal nuclease treatment step is included to remove contaminating DNA and mRNA from the original host cells. The extract is then dialyzed and stored frozen until needed.

The typical supplemental mix that is added to an S-30 coupled transcription and translation reaction contains buffers, such as Tris-acetate, dithiothreitol (DTT), the NTPs (ATP, CTP, GTP, and UTP), phosphoenol pyruvate, pyruvate kinase, amino acids (typically 10 of the 20 naturally occurring amino acids, leaving one out to permit addition of a radio-labeled amino acid or analog), polyethylene glycol (PEG), folinic acid, cAMP, tRNA, ammonium acetate, potassium acetate, calcium acetate and an optimized concentration of magnesium acetate. These types of components, or their equivalents, are mixed together in a process separate from the production of the S-30 extract. Supplemental mix is also typically stored frozen for later use in S-30 coupled reactions.

In the prior art a typical reaction conducted to produce in vitro protein from DNA using a *E. coli* S-30 extract involves the following components mixed together in a microcentrifuge tube, typically in a total volume of 25 to 50 microliters: 1. S-30 extract; 2. supplemental mix; 3. one or more additional amino acids (unlabeled or labeled); 4. water; and 5. the DNA template. This combination reaction is incubated for some period of time, typically an hour at 30–37° C. and the quantity and quality of the in vitro synthesized proteins is examined by a variety of methods.

BRIEF SUMMARY OF THE INVENTION

The present invention is summarized in that a method for the preparation of a fractionated *E. coli* S-30 reaction mixture for in vitro protein synthesis. The mixture is depleted in several macromolecules including the RNA degradsomes.

The present invention is also directed to the method of preparing this mixture, which involves the mixing of an S-30 extract and a supplemental mix in bulk to create a cloudy solution. This solution is then frozen, thawed and centrifuged. The supernatant is saved to form a clear uncloudy fractionated S-30 reaction mixture with enhanced performance features. The fractionated S-30 reaction mixture can be used to perform in vitro coupled transcription and translation reactions requiring fewer pipetting steps and giving a better result than obtained with standard S-30 extracts and reaction procedures.

It also is an object of the present invention to provide an *E. coli* S-30 protein synthesis system that produces a greater percentage of full length target protein and less non-full length target protein and noon-target protein than was possible using prior systems.

It is an object of the present invention to describe a method for preparing an *E. coli* S-30 transcription and translation reaction mixture that is superior to those previously known in the art both in ease of use and in performance.

It is an advantage of the present invention that the fractionated S-30 reaction mixture described here results in a higher yield of protein and a better fidelity of full length target protein produced than can be produced using prior art S-30 extract and supplements.

Other objects, advantages, and features of the present invention will become apparent from the following specification when taken in conjunction with the accompanying drawings.

DETAILED DESCRIPTION OF THE INVENTION

It has been found that if an *E. coli* S-30 extract is combined with a supplemental mix prior to use, and then fractionated, the combined and fractionated reaction mix can be used for in vitro protein synthesis procedures with results that are superior to prior S-30 formulations. The use of the improved partially purified, fractionated S-30 reaction mixture results in much less non-target protein, and less partial length protein synthesis, relative to the full length product, than prior art S-30 systems. In addition, the fractionated reaction mixture can be used in the protein synthesis process with fewer steps, greater efficiency and less chance for error.

It is difficult to identify all of the components which are removed from the S-30 extract in the fractionation step described here. However, analysis has revealed that the RNA degradosomes are largely removed from the extract. The removal of the RNA degradosomes, and the RNase E which is the organizing constituent of the degradosomes, is believed to be a significant contribution to the improved results obtained using a fractionated extract reaction mixture. Significant amounts of nucleic acids, both DNA and RNA, are also removed from the extract by this fractionation, and the removal of these components is also believed to contribute to the improved results.

As mentioned above, it is common practice in the art to provide separate S-30 extract and supplemental mix. The two solutions are then combined into a reaction mixture only at the time of performing the protein synthesis procedure. It is contemplated in the method and product described here that the two solutions are mixed together and fractionated prior to packaging, sale, and delivery to customer. Mixing a standard S-30 extract and a supplemental mix together results in a cloudy solution with precipitated material present. Here it is disclosed that if this combined solution is fractionated, as can be done by freezing and thawing this mix followed by centrifugation, the precipitated material can be removed without affecting the efficacy of the elements remaining in the supernatant. In fact, the performance of the material in the supernatant is superior to the performance of a corresponding non-fractionated mixture. In addition, the fractionated S-30 reaction mixture can be stored at −70° C. until needed for use in a protein synthesis reaction.

In a protein synthesis reaction, the product one wants from the reaction is the full-length target protein in as much abundance and with as much purity as it is practical to obtain. Most protein synthesis reactions using $E.\ coli$ S-30 extracts produce undesirable amounts of truncated or non-target proteins, due to a variety of factors such as endogenous protein-coding DNA and mRNA in the reaction mix and degradation of the transcribed mRNA by nucleases in the reaction mix originating from the extract. Scientists have used treatment of S-30 extract with calcium-dependent nuclease to remove endogenous DNA or mRNA, and pre-incubation of the extract to allow "run-off" of the ribosomes from endogenous mRNA. With prior techniques, however, it has not been possible to completely remove the DNA or mRNA without reducing extract protein synthesis activity to unacceptably low levels. It has been found now, quite surprisingly, that when such a reaction uses the partially purified fractionated S-30 reaction mixture described here, the full-length target protein is produced in much greater purity or, stated another way, there is much less production of truncated or non-target protein relative to the full-length protein. Western blotting or electrophoresis imaging techniques can easily visualize these improved results. Since the reaction described here uses a starting mixture formed from a combination of an S-30 extract and supplemental mix, the protein production process including this improvement actually involves less steps than the same procedure as performed in the prior art. In short, the process and product described here utilize both a better and an easier process and achieve superior results.

Again, in accordance with the prior procedures, various manufacturers have made and marketed $E.\ coli$ S-30 systems using the two separate constituents, S-30 extract and supplemental mix, which are combined only at the time of performing the protein synthesis reaction. Here it is contemplated that a combined fractionated S-30 reaction mixture will be sold as an item of commerce. The reaction mixture can be made by combining an S-30 $E.\ coli$ extract and supplemental mix, freezing and thawing the combination, and centrifuging the result to remove particulate matter. The resulting fractionated reaction mixture is a clear, not cloudy, solution that can be pre-made, and stored until needed. This reaction mixture product can thus be distributed in containers ready for use in bulk or in aliquots for individual reactions or groups of reactions. This product can be stored and shipped frozen, or potentially dried or lyophilized and rehydrated prior to use. This product is a new item of commerce that would make performing protein synthesis reactions with prokaryotic cell-free extracts more efficient and convenient than with prior art systems. The fractionated S-30 reaction mix can be stored in suitable containers for frozen or dried storage and for shipment to users. The mix can be accompanied by instructions for use and with accompanying constituents, such as pretested water and a positive control DNA, to form kits, a common practice in the industry.

Thus, in summary, one makes an $E.\ coli$ protein synthesis reaction mixture in accordance with the present invention by first culturing cells, harvesting them by centrifugation, and washing the resulting pellets. The cells are then re-suspended in a buffer and forced through a French press to lyse the cells. The lysed cells are then centrifuged twice to remove solid debris, after which the pre-incubation buffer is added to the extract and the result is incubated. Then a calcium salt is added, followed by the addition of micrococcal nuclease and incubation to degrade endogenous nucleic acids. Then EGTA is added to inactivate the nuclease, followed by dialysis against a dialysis buffer. The S-30 extract, which to this point is prepared by conventional procedures, can be frozen for storage, in aliquots if desired. Here, the procedure of the present invention diverges from standard protocols. The S-30 extract is then combined with the supplemental mix and an optimized concentration of magnesium. The S-30 reaction mixture, containing both S-30 extract and supplemental mix is then frozen in liquid nitrogen. When the reaction mix is thawed, the solution will be cloudy. Centrifugation at 16,000×g for 5 minutes removes the cloudiness from the mixture. The resulting fractionated S-30 reaction mixture is the supernatant recovered from this fractionation step. It can be dispensed into aliquots and frozen or dried until needed for use.

The main differences between the S-30 protein synthesis reaction mixture described here, and those in the prior art, are in the components which have been removed from this mixture by the fractionation process. Testing has demonstrated that the RNA degradosomes and endogenous DNA larger than about 2 kbp is size are preferentially removed from the S-30 protein synthesis reaction mixture of the present invention. Assaying for the RNase E and DNA levels in the mixture can test these attributes. In the preferred mixture in accordance with the present invention, native unmutated RNase E levels are decreased dramatically, to amounts difficult to visualize in Western blots using anti-RNase E antibody. The amount of endogenous DNA in the mix is reduced by something on the order of 90%, and certainly by more than 80%, while the amount of RNA in the mix is reduced by something on the order of 80%, while still retaining more than adequate protein synthesis capability.

In studying the nature of the constituents removed from the S-30 extract by the fractionation process described here, it was discovered that the presence of precipitation agent which preferentially causes precipitation of high molecular weight species is most helpful. In the typical S-30 protein synthesis reaction mixture, polyethylene glycol (PEG) is added as a part of the supplemental mixture, just prior to use of the extract for protein synthesis. PEG is separately sometimes used with salts to precipitate nucleic acids and has been used in the art to precipitate all of the macromolecular components of S-30 extracts as a means of concentration. Among the attributes of polyethylene glycol are that is makes large molecular weight constituents in a heterogeneous mixture more likely to precipitate. Under the condition used here, which include lower PEG and salt concentrations than have been used typically in the art for concentration, the extract is fractionated instead of merely concentrated. The fractionation selectively removes components that inhibit full-length protein synthesis and that cause synthesis of non-target proteins, while retaining active protein synthesis activity. It has been found here that the presence of polyethylene glycol, or some other precipitation agent for high molecular weight species, is preferable for obtaining the benefit of the fractionation process described here. Without including the polyethylene glycol, or some equivalent agent, the full benefit of the improvement to the S-30 protein expression kit is difficult to obtain. Other precipitation agents that have precipitation agent properties similar to PEG include polyethyleneimine (PEI), chitosan, and colloidal particles, such the Biocryl BPA series.

Note that it is believed that the steps of freezing and thawing are convenient for the fractionation process described here, but are not believed to be necessary. The precipitation agent PEG added by the supplemental mix to the extract makes the larger molecular weight components, such as large DNA molecules and the RNA degradosome complexes, less soluble. The freezing and thawing cycle appears to further reduce the solubility of those components. However, it is contemplated that a fractionation process based on one or more centrifugation steps or other similar separation processes will produce similar results.

As used herein, the term protein is used to signify both full-length biologically active proteins as well as inactive or truncated proteins, which some may prefer to term polypeptides, a term that is used occasionally herein as well.

To exemplify this improved process, an exemplary protocol for making and using the solutions used in the process is described below. All such variants of this exemplary protocol as come within the scope of the claims that follow are intended to be encompassed by this invention.

EXAMPLES

Making Stock Solutions.

1. Growth media: 5.6 g $KH_2PO_4$, 28.9 g $K_2PO_4$, 10 g yeast extract, 15 mg thiamine, water to 1 L; autoclave to sterilize; add 40 ml 25%(W/V) glucose/L media; add other vitamins according to strain requirements.
2. Wash buffer: 10 mM Tris-acetate, pH 8.0, 14 mM $Mg(OAc)_2$, 60 mM KCl, 1 mM DTT, 50 $\mu$g/ml PMSF; add PMSF just before use; store at 4° C.
3. Lysis buffer: 10 nmM Tris-acetate, pH 8.0, 14 mM $Mg(OAc)_2$, 60 mM KCl, 50 Fg/ml PMSF; add PMSF just before use, store at 4° C.
4. Preincubation buffer: Immediately prior to use, prepare solution containing 3.75 ml 2 M Tris-acetate, pH 8.0, 236.7 $\mu$l 1.0 M $Mg(OAc)_2$, 75 $\mu$l 1 M DTT, 75 $\mu$l 10 mM amino acids mixture, 600 $\mu$l 0.1 M ATP, 0.2 g phosphoenol pyruvate (trisodium salt), 50 units (25 $\mu$l) pyruvate kinase, 4.99 ml water.
5. 0.1 M $CaCl_2$, filtered with 0.2$\mu$ filter and stored at 4° C.
6. 0.2 M EDTA, filtered with 0.2$\mu$ filter and stored at 4° C.
7. 178.6 units/$\mu$l microccocal nuclease, stored at −20° C.
8. Dialysis buffer: 10 mM Tris-acetate, pH 8.0, 14 mM $Mg(OAc)_2$, 60 mM KOAc, 1 mM DTT, 50 $\mu$g/ml PMSF. Add the PMSF just prior to use, store at 4° C.

Supplemental Mix.

The supplemental mix was prepared by adding the following constituents in the following proportions.

| Components | Concentration in Buffer |
| --- | --- |
| 2.0 M Tris-acetate, pH 8.2 | 87.6 mM |
| 5.0 M Potassium glutamate | 525 mM |
| 3. M Ammonium acetate | 83.7 mM |
| 1.0 M DTT | 5 mM |
| 4.0 mM Amino acids mix-methione | 0.25 mM |
| 0.1 M ATP | 5.5 mM |
| 0.1 M CTP | 1.377 mM |
| 0.1 M GTP | 1.377 mM |
| 0.1 M UTP | 1.377 mM |
| Phosphoenol pyruvate (trisodium salt) | 110 mM |
| 27.5 mg/ml *E. coli* tRNA | 0.253 mg/ml |
| 50% (w/v) PEG (8000 mol. wt) | 117.5 mg/ml |
| 2.7 mg/ml Folinic acid | 0.055 mg/ml |
| 50 mM cAMP | 2.5 mM |

Culturing Cells.

The preferred strains of *E. coli* are SL 119 and SL 119(DE3)LacZ. A streak is made from a glycerol stock onto an LB plate containing 12.5 $\mu$g/ml tetracycline. The plate is incubated at 37° C. overnight.

A single colony is picked from the overnight plate and inoculated into 50 ml of LB medium with 12.5 $\mu$g/ml tetracycline. The culture is incubated overnight at 37° C. with shaking at 250 rpm.

On the following day, 50 ml of the overnight culture is inoculated into 900 ml of growth medium plus 12.5 $\mu$g/ml tetracycline and incubated at 37° C. with shaking at 250 rpm. The growth is monitored at 30 minute intervals by measuring optical density at 600 nm. When the optical density value is 2.0 to 3.0, transfer 6 aliquots of 150 ml of culture into 2.8 liter Fernbach flasks containing 850 ml of growth medium, which are then incubated at 37° C. with vigorous shaking with monitoring of growth by optical density. When the density values in these cultures measured at 600 nm is 0.8 to 1.0 with a 1/5 dilution of the culture, the cultures are immediately transferred to ice water and rapidly chilled with swirling.

For the SL119(DE3) cultures, the optical density at 600 nm is allowed to reach 1.5 to 2.0 without dilution, and IPTG is added to a final concentration of 0.5 mM in each of the flasks, which are then incubated for an additional 2–3 hours at 37° C. before transfer to the ice water.

The cells are harvested by centrifugation at 3500 g for 10 minutes at 4° C. The cell pellets are saved, and are re-suspended in a total of 2 L of wash buffer, followed by centrifugation at 3500 g for 10 minutes at 4° C. Again the cell pellets are saved, re-suspended in 2 L of wash buffer and centrifuged at 16,000 g for 20 minutes at 4° C., and the cell pellets saved. The cell pellets are combined and can be processed immediately or stored at −70° C.

Preparation of Extract.

The cell pellets are re-suspended thoroughly in cold lysis buffer at a ratio of 2 ml of buffer per gram of cells. The cells are passed through a 22-gauge needle for complete re-suspension. The cells are then lysed by passage through a chilled French pressure cell at 8,000–10,000 psi. DTT is immediately added to the lysate to yield a final concentration of 1 mM.

The lysed cells are then centrifuged at 30,000 g for 10 minutes at 4° C. The supernatant is saved and transferred to a clean centrifuge tube. The supernatant is then centrifuged at 46,000 g for 20 minutes at 4° C. and the supernatant is removed and transferred to a clean flask on ice and is measured for volume.

One ml of pre-incubation buffer is added for every 6.5 ml of the S-30 extract, followed by gentle shaking for 60 minutes at 30–32° C. Then $CaCl_2$ is added to a final concentration of 1 mM and microccocal nuclease to a final concentration of 1.32 units per ml, followed by incubation for 30 minutes at 26° C. EGTA is then added to a final concentration of 2 mM, followed by mixing and the mixture is placed on ice.

The S-30 extract is then transferred to dialysis tubing (mol. wt. cut-off 6,000–8,000) and dialyzed against 4 L of cold dialysis buffer at 4° C. The buffer is changed three times at one hour intervals. The resulting S-30 extract is divided into aliquots, frozen in liquid nitrogen and stored at −70° C.

Optimization.

As with any protein synthesis system, it is then appropriate to optimize the concentration of magnesium salt for the reaction. This is done by varying the concentration of magnesium ions in small test reactions until an optimum is reached. Small aliquots of S-30 extract are thawed, as are small aliquots of supplemental mix. 0.3 ml of S-30 extract is combined with 0.4 ml of supplemental mix followed by mixing (to make the reaction mix) and freezing in liquid nitrogen. The combined material is thawed on ice and put in the microcentrifuge where it is spun at 14,000 rpm for 5 minutes at 4° C. The supernatant is removed and placed on ice. This supernatant is the fractionated S-30 reaction mixture which is then used in test protein synthesis reactions. Parallel reactions are conducted using varying amounts of magnesium salts in the test reactions in the range of 5 to 15 mM of added magnesium, until the optimum magnesium value is determined for that batch of reaction mixture. A typical optimal magnesium concentration is 10.6 mM magnesium acetate Making the Bulk Fractionated S-30 Reaction Mixture.

The bulk S-30 extract and the bulk supplemental mix are thawed. The two solutions are combined at a ratio of 0.75 ml of S-30 extract for each 1 ml of supplemental mix (or the ratio is based on the optimized ratio), followed by mixing at 4° C. Magnesium acetate is added sufficient to bring the magnesium concentration to the level determined by the optimization step, followed by more mixing at 4° C. The combined mixture is then frozen on liquid nitrogen. After freezing, the material is thawed and spun at 16,000 g for 5 minutes at 4° C. for fractionation. The supernatant is removed and separated into aliquots as desired for particular reaction sizes, and frozen and stored until use. This is the fractionated S-30 reaction mixture.

Coupled Protein Synthesis Reactions.

The frozen aliquots are thawed and used in a coupled transcription and translation protein synthesis reaction. A typical reaction uses 35 µl of the fractionated S-30 reaction mixture with labeled or unlabeled methionine, plus a DNA template, plus water to bring the volume to 50 µl. The reaction is incubated for 60 minutes at 37° C. The production of reaction products can be assayed by any of a variety of techniques including gel electrophoresis separation and detection by radioactive, immunological or enzymatic techniques well known to the art.

Exemplary Results.

Using the reagents and protocols described above, protein synthesis reactions have been repeatedly performed. One set of reactions was conducted using the improved fractionated S-30 reaction mixture, as described above, in parallel with the same reactions conducted using the same reagents, except that the S-30 extract and the supplemental mix were not combined and fractionated prior to use. In other words, this experiment compared the partially purified reaction mix of the present invention with the prior art methods for S-30 reactions. To properly sample the prior art, three different commercial S-30 extracts were used from two different manufacturers, Ambion PROTEINscript-PRO, Promega *E. coli* S30 Extract System for Linear Templates, Promega *E. coli* S30 extract System for Circular DNA.

Figure 1:
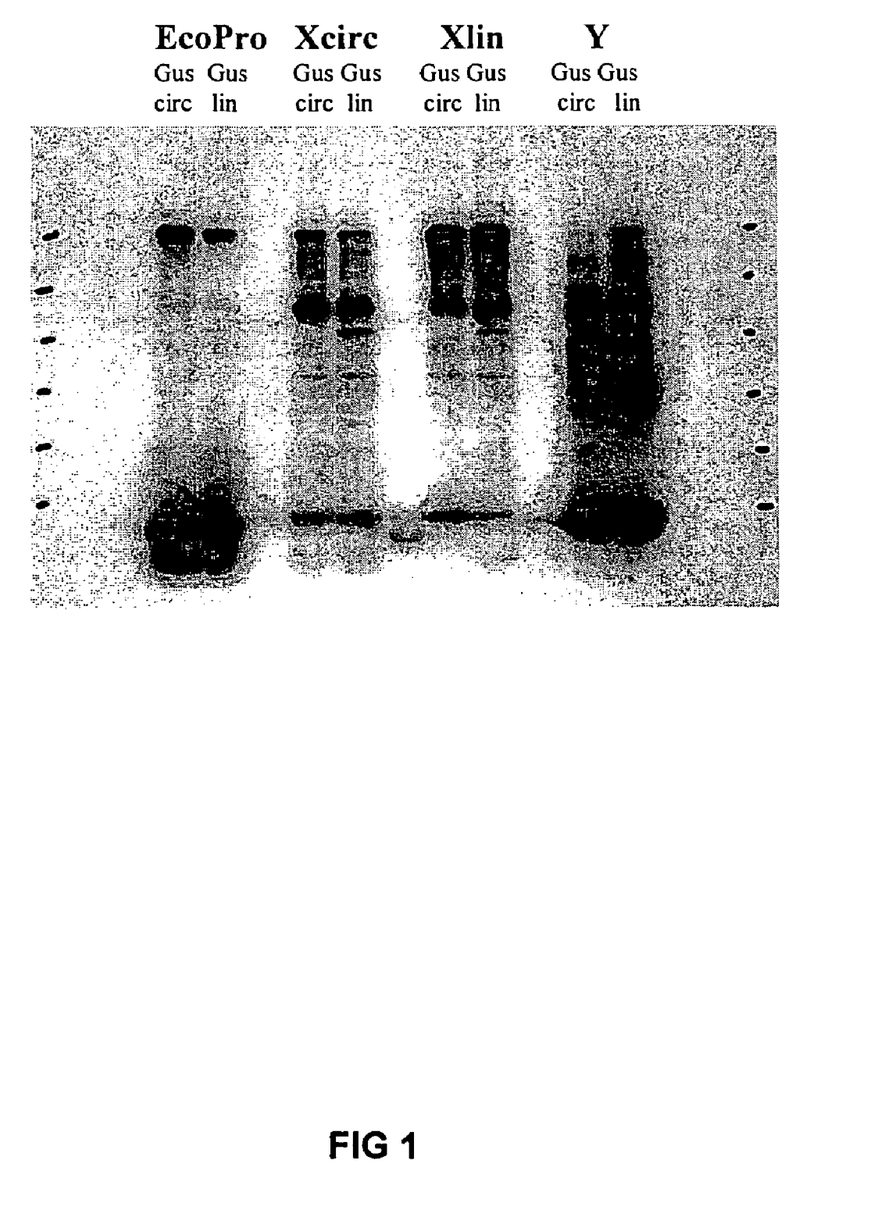
FIG. 1 is an autoradiograph of research results from an experiment recited in the examples below.

The template DNA used was a construct encoding the expression of the protein β-glucuronidase under the control of an *E. coli* tac promoter. The DNA was used in both circular form and as a linear PCR product amplified with primers flanking the promoter and coding regions. The reactions included $^{35}$S-methionine as a radioactive label. The resulting proteins were size separated on an electrophoresis gel and a reproduction of the autoradiograph of that gel is attached hereto as FIG. 1. In FIG. 1, the first three columns show the results from the use of an extract (EcoPro) according to the present invention, with circular (C), linear PCR (P) and no template (−). The next two sets of three lanes are the Promega S30 circular system (Xcirc) and the Promega S30 linear DNA system (Xlin), with the same templates. The last three columns are the Ambion S30 system (Y), again with the same three templates.

The results demonstrate better quantity of full length target protein expression and better fidelity of expression than the prior art systems. Using a variety of protein products and DNA templates, more target protein and less non-target protein was produced using this improved fractionated S-30 reaction mixture than could be achieved using prior art procedures. The results tended contrast to the prior art S-30 systems which typically result not only in less target protein production, but also abundant production of non-target protein.

Characterization of Fractionated S-30 Reaction Mix.

Figure 2:
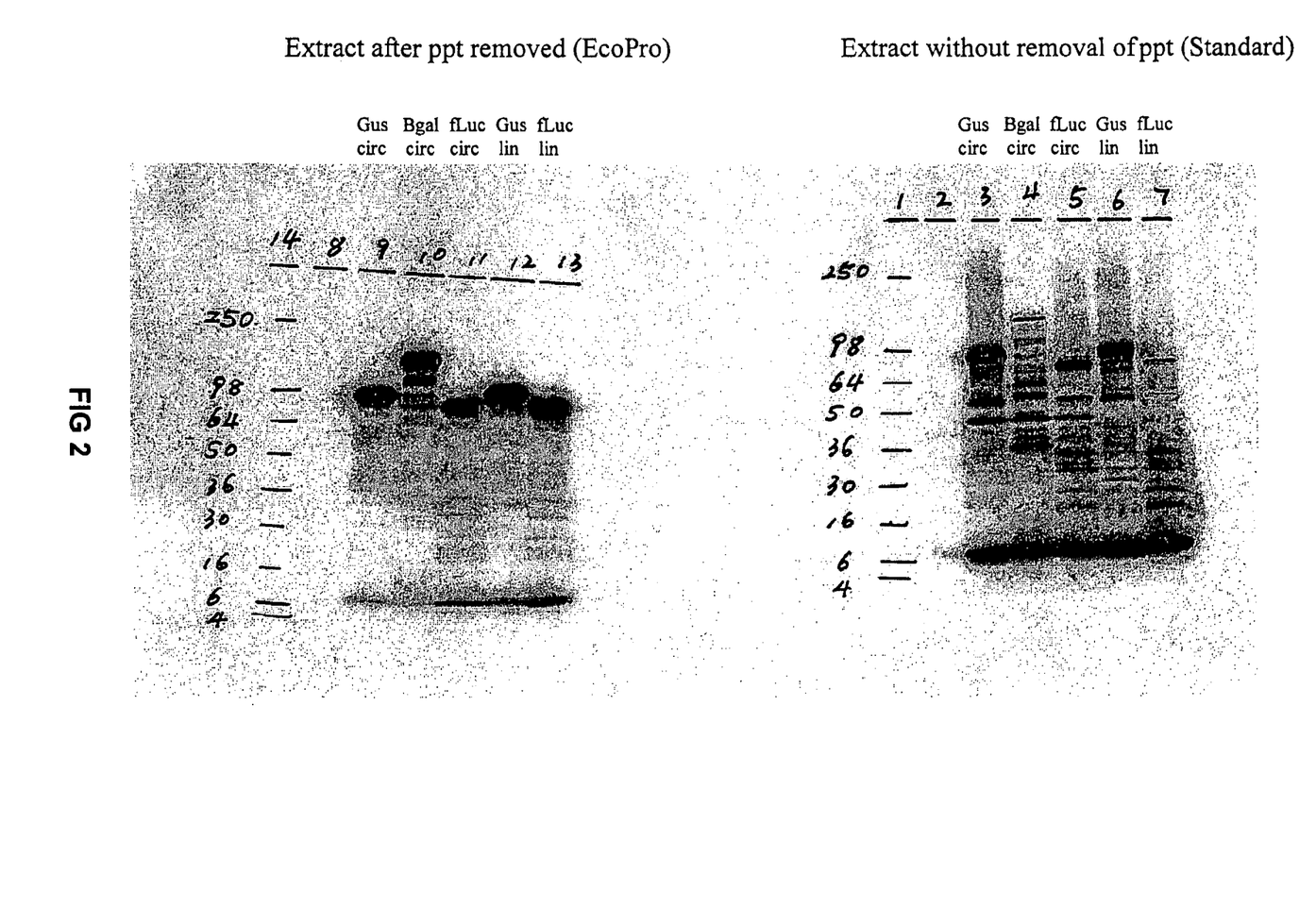
FIG. 2 is another autoradiograph illustrating results from experiments described in the examples.

In order to better understand the nature of what components are removed from an *E. coli* protein synthesis system by the fractionation procedure described here, a series of tests were conducted. First, a test was conducted to confirm that the post-freezing separation by centrifugation is responsible for the improved results. To perform this test, protein expression experiments were conducted with two sets of S-30 reaction mixes. One set was prepared as described above, including the fractionation step of freezing, thawing, and centrifuging the combined S-30 extract and the supplemental mix. The second set of reaction mixes was the combined S-30 extract and supplemental mix that was not subjected to post-mixing fractionation. The same templates were then used as templates in protein synthesis reactions using both reaction mixes in the presence of $^{35}$S-methionine to label the synthesized proteins. The results can be seen in the autoradiograph of FIG. 2. The samples in the left-hand gel in FIG. 2 were the fractionated S-30 reaction mixture, while the samples in the right-hand gel is FIG. 2 were done with the reaction mix without the fractionation step. The templates used were β-glucuronidase (Gus), β-galactosidase (Bgal), and firefly luciferase (fLuc). As can be seen by looking at the gels shown in FIG. 2, the reactions performed with the fractionated S-30 reaction mixtures exhibit a much cleaner pattern, indicating less non-target protein production that the reactions performed with the conventional reaction mix. Yet the bands for the target protein actually appear denser and stronger in the reactions performed with the fractionated S-30 reaction mixtures. In other words, the results are much better with the fractionated S-30 reaction mixture.

Figure 3:
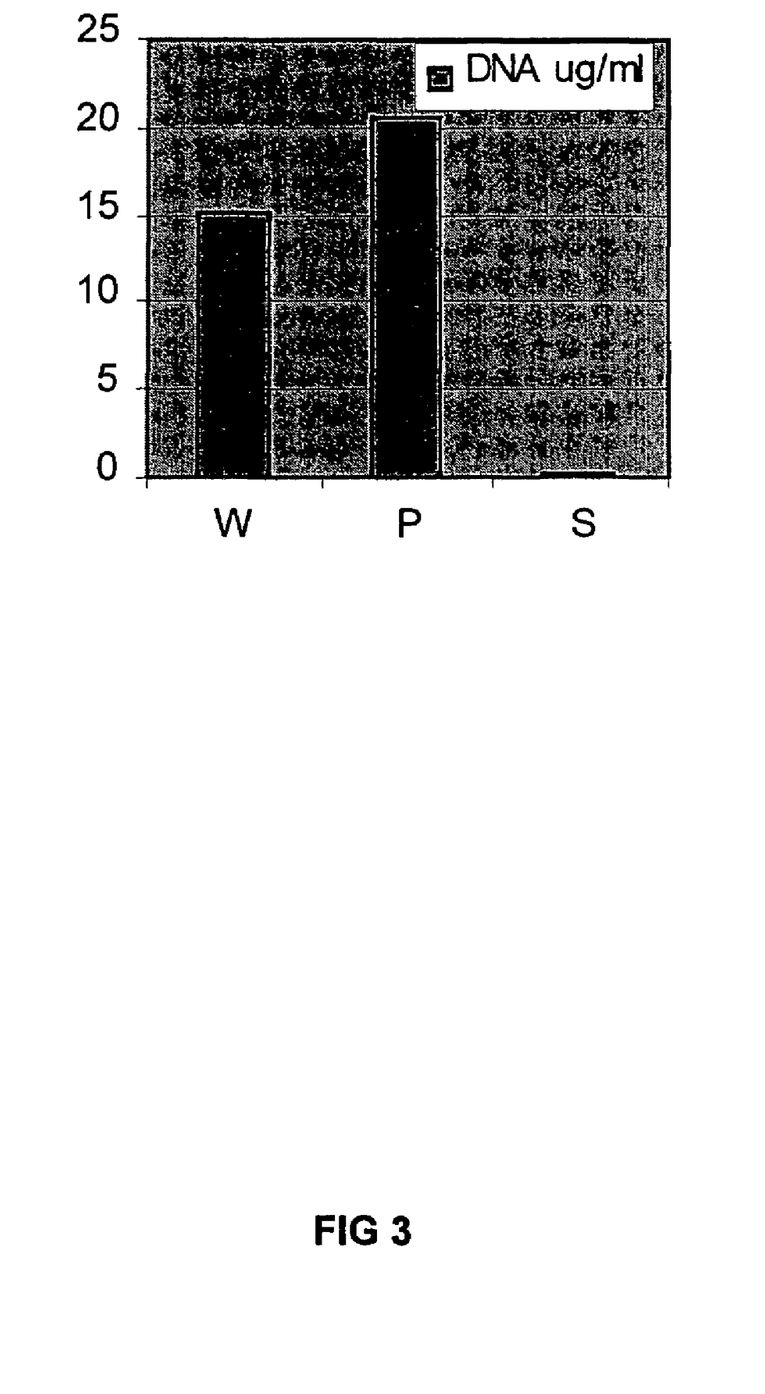
FIG. 3 is a histogram illustrating results from the examples.
Figure 4:
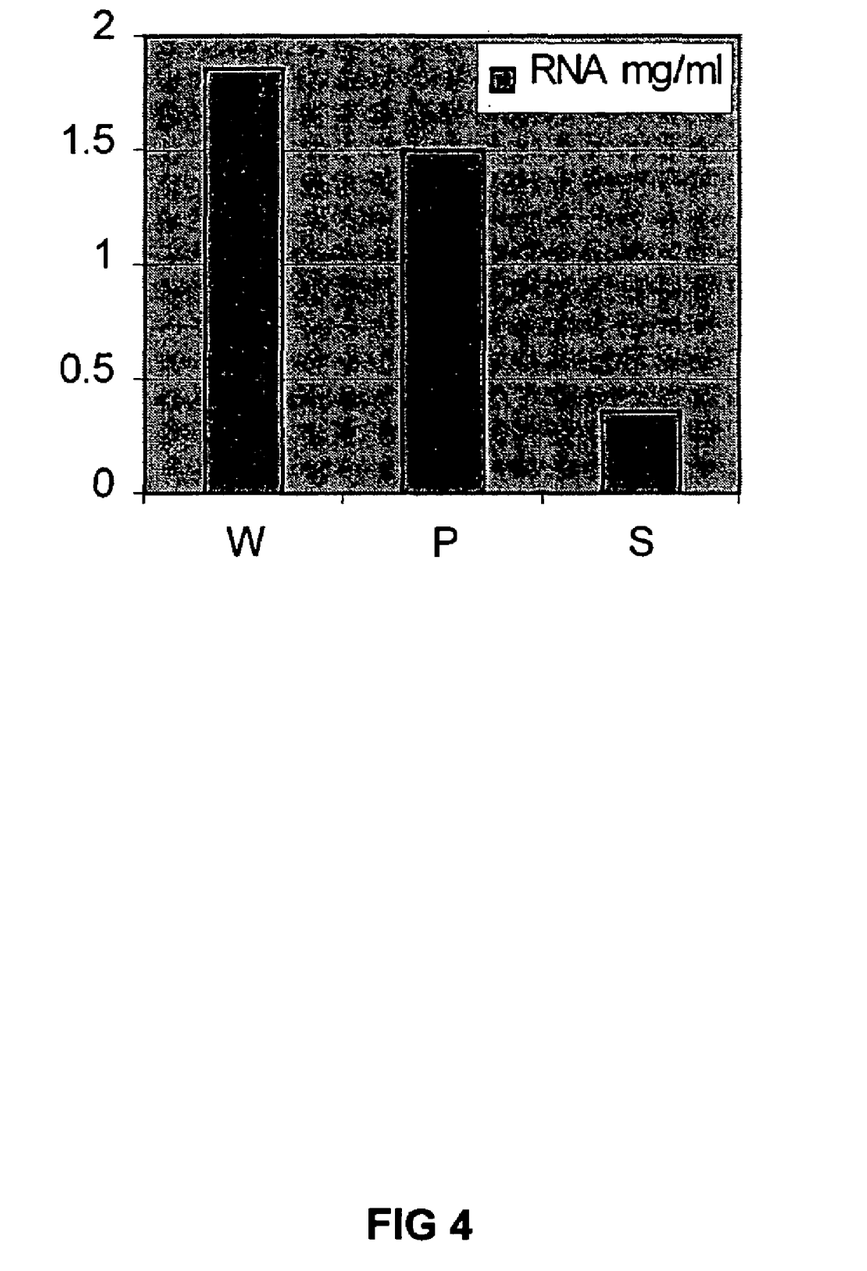
FIG. 4 is another histogram of experimental results.
Figure 5:
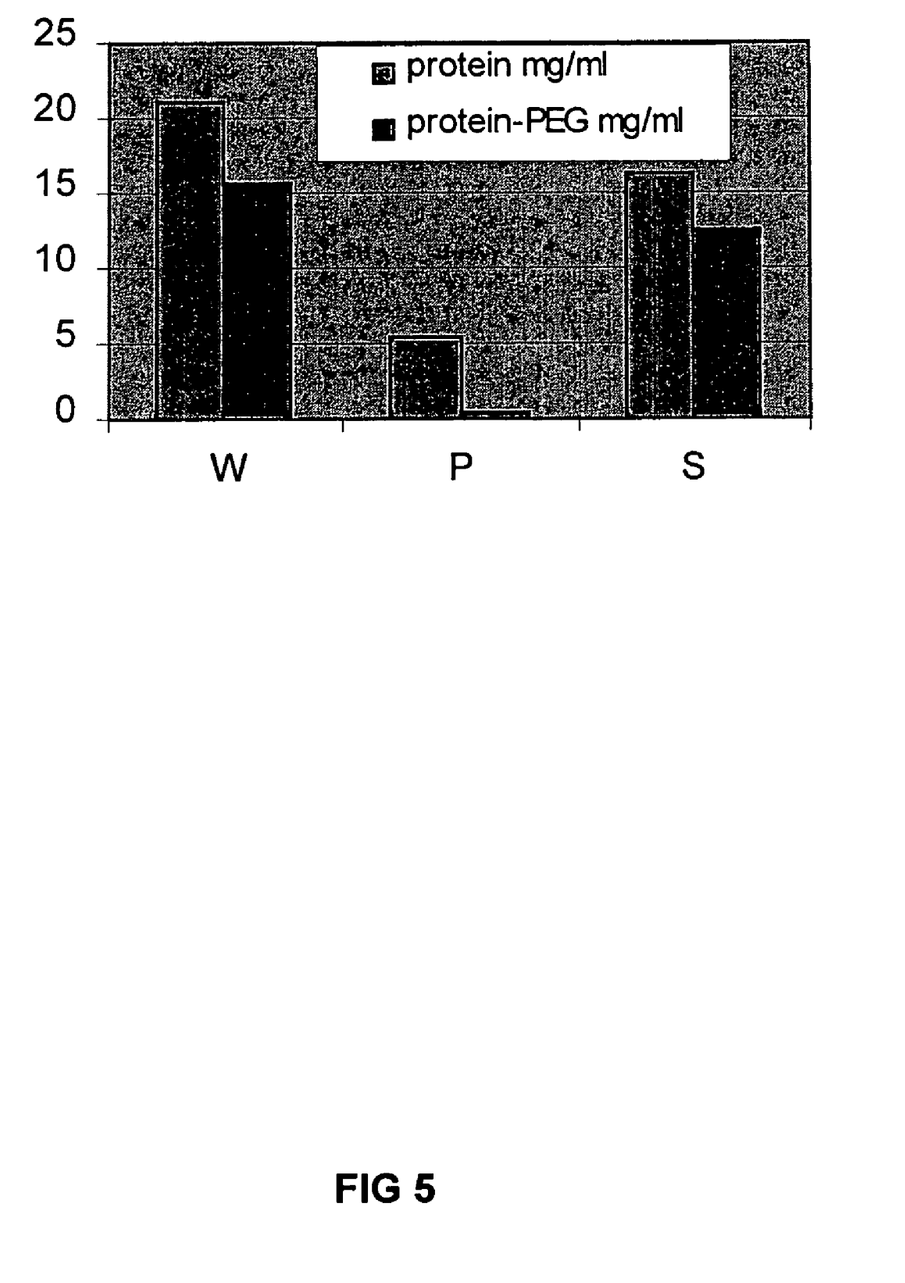
FIG. 5 is yet another histogram of experimental results.

A series of measurements of total DNA, total RNA and total protein as changed in the mix by the fractionation step was then conducted. Nucleic acid content was measured following extraction of the respective samples with phenol to remove protein, which may interfere with the assays. Total DNA was measured after RNase treatment using the PicoGreen commercial kit (Molecular Probes). Total RNA was measured using the PicoGreen commercial kit (Molecular Probes). Total protein was measure using the BCA commercial kit (Pierce Chemical Co.). The results are summarized in the histograms contained in FIGS. 3 to 5. In each figure, the "W" indicates the whole S-30 extract reaction mix, without fractionation, the "P" indicates the content of the precipitate or pellet, re-suspended in water following centrifugation of the freeze-thawed mixture of the S-30 extract and the supplemental mix. Also in these figures, the "S" indicates the content of the supernatant, which is the fractionated S-30 reaction mixture. As can be seen in FIG. 3, the amount of DNA in the pellet actually measured to be more than in the whole extract (likely due to improved recovery following phenol extraction of the sample in the pellet). Very little DNA remained in the supernatant, i.e. in the fractionated S-30 reaction mixture. In FIG. 4, the results demonstrate that over 80% of the total RNA is in the pellet or precipitate and is removed from the mix by the fractionation step. This result is somewhat surprising since obviously the various rRNA species are all needed for protein synthesis, yet still target protein synthesis using the supernatant is actually increased relative to the whole extract. In FIG. 5, the results seem to indicate that only about one-quarter of the protein in the whole extract is removed by the fractionation step. Analysis of the proteins in the various samples by SDS-polyacrylamide gel electrophoresis reveals that a number of proteins are selectively removed from the extract by the fractionation procedure.

Figure 6:
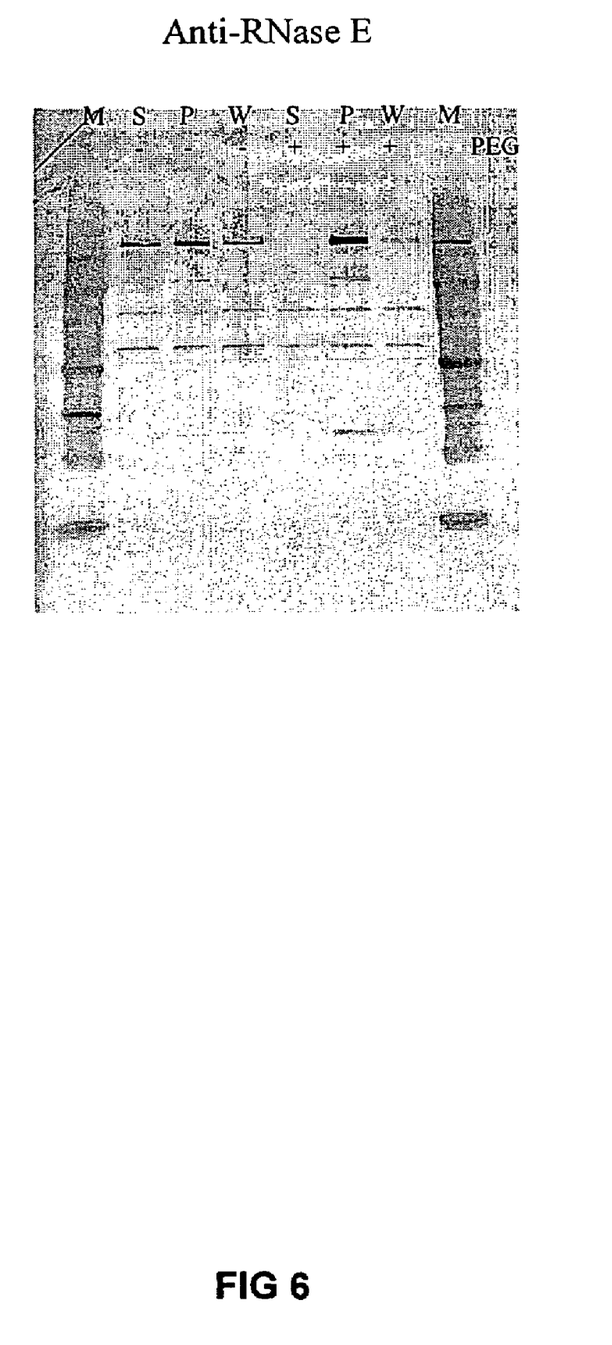
FIGS. 6 and 7 are more autoradiographs of experimental results.

An analysis was also undertaken to verify the suspicion that the RNA degradosomes were being removed by the fractionation process, and that the present of the precipitation agent is important in that removal. Shown in FIG. 6 is a western blot using an anti-RNase E antibody to probe a non-fractionated reaction mix ("W"), the re-suspended precipitate from the fractionation step ("P") and the supernatant from the fraction step ("S"), all prepared similarly to the ones described just above. No protein synthesis was performed for this analysis, the mixtures themselves were being analyzed. In addition, parallel preparations were made omitting the PEG (PEG– in FIG. 6) and including the normal PEG (PEG+ in FIG. 6). In the gel, size markers appear in the lanes on each side. By comparing the sets of three lanes, it can readily be seen that there is no, or at least very little, material binding to the anti-RNase E antibody in the supernatant, but only in the preparation including the PEG. If the PEG is omitted from the preparation, the fractionation does not remove from the supernatant the molecules that bind the antibody. Thus, this data demonstrates that the fractionation step is efficient, in the presents of the precipitation agent, for removing RNA degradosomes from the reaction mixture, RNase E being the organizing components of those complexes. This may account for the improved production of target protein in the fractionated reaction mixture of the present invention.

Figure 7:
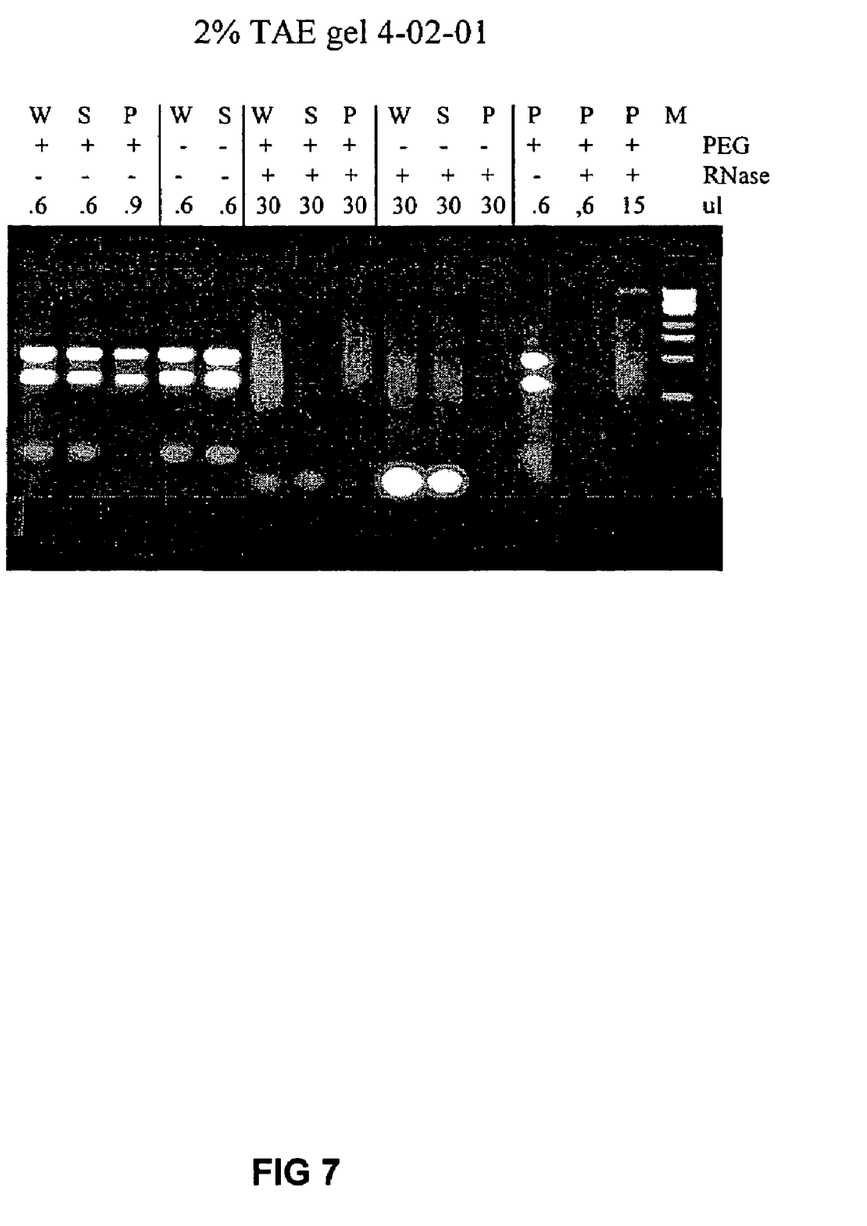

Shown in FIG. 7 is an analysis of DNA content of the same solutions, again using the nomenclature of W for the non-fractionated mixture, P for re-suspended precipitate from the fractionation procedure and S for supernatant from the fractionation. In FIG. 7, size separated DNA is visualized. On the right of the image, three row labels are present, "PEG", "RNase" and "ul". The row labeled "PEG" indicates the presence or absence of PEG in the preparation. The row labeled "RNase" indicated whether or not the mixture was treated with RNase prior being run on the gel. The row label "ul" refers to the number of microliters of the appropriate solution that was loaded onto the gel. Again no protein synthesis was performed, and no DNA template was added. The most significant results are observed in the middle six lanes, all with RNase treatment, the left-hand three being with PEG while the right-hand three were without PEG. Note that in the presence of PEG, almost all the longer DNA species migrated into the precipitate and very little is in the supernatant. Note, by comparison, that in the three lanes for the preparations in which PEG was not added, no such removal of DNA from the supernatant is apparent. The combination of the use of the precipitation agent and the freezing and centrifugation process appears to remove an significant and potentially important amount of the endogenous DNA from the reaction mixture as compared with prior art mixtures.

We claim:

1. A reaction mixture comprising an *E. coli* S-30 extract combined with a supplemental mix comprising buffer, salts, nucleoside triphosphates, and an energy source, the S-30 extract prepared by the process of
    (a) growing *E. coli* cells in culture;
    (b) collecting the cells;
    (c) resuspending the cells in an aqueous solution;
    (d) processing the resuspended cells to release their contents by lysis, and
    (e) centrifuging the cell lysate, the supernatant being the S-30 extract;
    wherein the reaction mixture, after preparation, is further processed by the step of fractionating the reaction mixture by freezing, thawing and centrifugation.

2. A reaction mixture comprising an *E. coli* extract containing *E. coli* transcriptional and translational components combined with a supplemental mix comprising buffer, salts, nucleoside triphosphates and an energy generating system, wherein the *E. coli* extract is the supernatant of lysed and centrifuged *E. coli* cells, the reaction mixture having the degradosomes substantially removed therefrom.

3. The reaction mixture of claim 2 wherein the supplemental mix further comprises amino acids.

4. The reaction mixture of claim 2 wherein the supplemental mix further comprises phosphoenol pyruvate.

5. The reaction mixture of claim 2 wherein the supplemental mix further comprises polyethylene glycol.

6. The reaction mixture of claim 5 wherein the polyethylene glycol is PEG 8000.

7. The reaction mixture of claim 2 further comprising T7 RNA polymerase.

8. The reaction mixture of claim 2 wherein the reaction mixture is frozen.

9. The reaction mixture of claim 2 wherein the reaction mixture is dried.

10. A method of making the reaction mixture of claim 2 comprising
   (a) lysing *E. coli* cells and centrifuging the lysate to produce an *E. coli* extract;
   (b) combining the *E. coli* extract with a supplemental mix to form a combined solution, wherein the supplemental mix comprises buffer, salts, nucleoside triphosphates, an energy generating system, and a precipitating agent that preferentially precipitates high molecular weight molecules;
   (c) centrifuging the combined solution and separating the supernatant to make the reaction mixture.

11. The method of claim 10 wherein the precipitating agent is polyethylene glycol, polyethyleneimine, or colloidal particles.

12. The method of claim 10 wherein the precipitating agent is polyethylene glycol.

13. The method of claim 10 wherein the polyethylene glycol is PEG 8000.

14. The method of claim 10 further comprising treating the *E. coli* extract with micrococcal nuclease to degrade endogenous nucleic acids.

15. The method of claim 10 further comprising freezing and thawing the combined solution prior to step (c).

16. The method of claim 10 wherein the *E. coli* cells are cultured with isopropyl β-D-1-thiogalactopyranoside prior to lysis.

17. The method of claim 10 further comprising placing the reaction mixture into containers for commercial sale.

* * * * *

UNITED STATES PATENT AND TRADEMARK OFFICE
CERTIFICATE OF CORRECTION

| | |
|---|---|
| PATENT NO. | : 7,008,651 B2 |
| APPLICATION NO. | : 09/848449 |
| DATED | : March 7, 2006 |
| INVENTOR(S) | : Yuping Ambuel, Robert C. Mierendorf and Thomas Van Oosbree |

It is certified that error appears in the above-identified patent and that said Letters Patent is hereby corrected as shown below:

Column 7, line 65: Replace "10 nmM Tris-acetate," with --10 mM Tris-acetate,--.

Col. 2, line 64: Replace "proteases have also be used" with --proteases have also been used--.

Col. 4, line 10: Replace "The present invention is summarized in that a method for. . ." with -- The present invention is summarized as a method for…--.

Col. 7. line 15: Replace "is makes large molecular weight constituents" with -- it makes large molecular weight constituents--.

Col. 11, line 6: Replace "the samples in the right-hand gel is FIG. 2" with --the samples in the right-hand gel in FIG. 2--.

Col. 11, lines 12-13: Replace "indicating less non-target protein production that the reactions performed ..." with --indicating less non-target protein production than the reactions performed…--.

Col. 11, line 27: Replace "Total protein was measure with" with --Total protein was measured with--.

Col. 11, lines 56-57: Replace "and that the present of the precipitation agent is important…" with --and that the present precipitation agent is important…--.

Col. 12. line 7: Replace "in the presents of the precipitation agent," with --in the presence of the precipitation agent,--.

UNITED STATES PATENT AND TRADEMARK OFFICE
CERTIFICATE OF CORRECTION

| | | |
|---|---|---|
| PATENT NO. | : 7,008,651 B2 | |
| APPLICATION NO. | : 09/848449 | |
| DATED | : March 7, 2006 | |
| INVENTOR(S) | : Yuping Ambuel, Robert C. Mierendorf and Thomas Van Oosbree | |

It is certified that error appears in the above-identified patent and that said Letters Patent is hereby corrected as shown below:

<u>Col. 12. lines 36-37:</u>  Replace "appears to remove an significant and potentially important amount" with --appears to remove a significant and potentially important amount--.

Signed and Sealed this

Twenty-first Day of November, 2006

JON W. DUDAS
*Director of the United States Patent and Trademark Office*